(12) United States Patent
Avey et al.

(10) Patent No.: US 12,327,615 B2
(45) Date of Patent: *Jun. 10, 2025

(54) GENETIC COMPARISONS BETWEEN GRANDPARENTS AND GRANDCHILDREN

(71) Applicant: 23andMe, Inc., Sunnyvale, CA (US)

(72) Inventors: Linda Avey, Lafayette, CA (US); Oleksiy Khomenko, Stanford, CA (US); Brian Thomas Naughton, Mountain View, CA (US); Serge Saxonov, Oakland, CA (US); Anne Wojcicki, Palo Alto, CA (US); Alexander Wong, Palo Alto, CA (US)

(73) Assignee: 23andMe, Inc., Sunnyvale, CA (US)

( * ) Notice: Subject to any disclaimer, the term of this patent is extended or adjusted under 35 U.S.C. 154(b) by 898 days.

This patent is subject to a terminal disclaimer.

(21) Appl. No.: 17/449,081

(22) Filed: Sep. 27, 2021

(65) Prior Publication Data

US 2022/0157405 A1 May 19, 2022

Related U.S. Application Data

(63) Continuation of application No. 15/829,782, filed on Dec. 1, 2017, now Pat. No. 11,170,873, which is a continuation of application No. 12/288,026, filed on Oct. 15, 2008, now Pat. No. 9,864,835.

(60) Provisional application No. 60/999,065, filed on Oct. 15, 2007.

(51) Int. Cl.
| | |
|---|---|
| *G16B 45/00* | (2019.01) |
| *G16B 10/00* | (2019.01) |
| *G16B 20/00* | (2019.01) |
| *G16B 20/20* | (2019.01) |
| *G16B 20/40* | (2019.01) |
| *G16B 30/00* | (2019.01) |

(52) U.S. Cl.
CPC ............ *G16B 45/00* (2019.02); *G16B 20/20* (2019.02); *G16B 20/40* (2019.02); *G16B 10/00* (2019.02); *G16B 20/00* (2019.02); *G16B 30/00* (2019.02)

(58) Field of Classification Search
CPC ............ C12Q 2600/156; C12Q 1/6883; C12Q 2600/172; C12Q 1/6827; C12Q 2537/165; C12Q 2600/112; C12Q 2600/118; C12Q 2600/124; G16B 20/20; G16B 20/00; G16B 20/40; G16B 40/00; G16B 30/00; G16B 50/00; G16B 30/10; G16B 45/00; G16B 50/30; G16B 50/10; G16B 5/20; G16H 50/20; G16H 50/30; G16H 10/60; G16H 50/70; G16H 50/50; G16H 70/60; G06N 7/01; G01N 2800/50
See application file for complete search history.

(56) References Cited

U.S. PATENT DOCUMENTS

| | | |
|---|---|---|
| 5,376,526 A | 12/1994 | Brown et al. |
| 6,750,011 B1 | 6/2004 | Perlin |
| 6,812,339 B1 | 11/2004 | Venter et al. |
| 7,797,302 B2 | 9/2010 | Kenedy et al. |
| 7,818,281 B2 | 10/2010 | Kennedy et al. |
| 7,818,310 B2 | 10/2010 | Kenedy et al. |
| 7,844,609 B2 | 11/2010 | Kenedy et al. |
| 7,917,438 B2 | 3/2011 | Kenedy et al. |
| 7,933,912 B2 | 4/2011 | Kenedy et al. |
| 7,941,329 B2 | 5/2011 | Kenedy et al. |
| 7,941,434 B2 | 5/2011 | Kenedy et al. |
| 7,957,907 B2 | 6/2011 | Sorenson et al. |
| 8,024,348 B2 | 9/2011 | Kenedy et al. |
| 8,051,033 B2 | 11/2011 | Kenedy et al. |
| 8,055,643 B2 | 11/2011 | Kenedy et al. |
| 8,065,324 B2 | 11/2011 | Kenedy et al. |
| 8,099,424 B2 | 1/2012 | Kenedy et al. |
| 8,108,406 B2 | 1/2012 | Kenedy et al. |
| 8,185,461 B2 | 5/2012 | Kenedy et al. |
| 8,187,811 B2 | 5/2012 | Eriksson et al. |
| 8,200,509 B2 | 6/2012 | Kenedy et al. |
| 8,209,319 B2 | 6/2012 | Kenedy et al. |
| 8,224,835 B2 | 7/2012 | Kenedy et al. |
| 8,255,403 B2 | 8/2012 | Kenedy et al. |
| 8,326,648 B2 | 12/2012 | Kenedy et al. |
| 8,386,519 B2 | 2/2013 | Kenedy et al. |
| 8,428,886 B2 | 4/2013 | Wong et al. |
| 8,452,619 B2 | 5/2013 | Kenedy et al. |

(Continued)

FOREIGN PATENT DOCUMENTS

| | | |
|---|---|---|
| CA | 2632230 C | 5/2019 |
| WO | 2006036735 A2 | 4/2006 |

(Continued)

OTHER PUBLICATIONS

International Search Report and Written Opinion, PCT Application PCT/US2008/011806, mailed Dec. 10, 2008.
International Search Report and Written Opinion, PCT Application PCT/US2008/011833, mailed Dec. 29, 2008.
Lightfoot et al. Quantitative trait loci associated with maximal exercise endurance in mice. (2007) J Applied Physiol. vol. 103, p. 105-110. (Year: 2007).
Notice of Allowance, U.S. Appl. No. 18/198,699, mailed Sep. 28, 2023.
Office Action, U.S. Appl. No. 18/198,699, mailed Aug. 15, 2023.
U.S. Notice of Allowance dated Jun. 18, 2021 in U.S. Appl. No. 15/829,782.

(Continued)

*Primary Examiner* — Mary K Zeman
(74) *Attorney, Agent, or Firm* — McDonnell Boehnen Hulbert & Berghoff LLP; David K. Buckingham

(57) ABSTRACT

Displaying a comparison of genotypic information between relatives is disclosed, including receiving an indication that a first individual is a grandparent, receiving an indication that a second individual is a grandchild of the first individual, comparing the genotypic information of the first individual and the second individual and calculating a similarity score, and displaying an indication of the similarity score graphically using colors.

42 Claims, 10 Drawing Sheets
(7 of 10 Drawing Sheet(s) Filed in Color)

(56) References Cited

U.S. PATENT DOCUMENTS

| | | |
|---|---|---|
| 8,458,097 B2 | 6/2013 | Kenedy et al. |
| 8,458,121 B2 | 6/2013 | Kenedy et al. |
| 8,463,554 B2 | 6/2013 | Hon et al. |
| 8,510,057 B1 | 8/2013 | Avey et al. |
| 8,543,339 B2 | 9/2013 | Wojcicki et al. |
| 8,589,437 B1 | 11/2013 | Khomenko et al. |
| 8,606,761 B2 | 12/2013 | Kenedy et al. |
| 8,645,343 B2 | 2/2014 | Wong et al. |
| 8,655,899 B2 | 2/2014 | Kenedy et al. |
| 8,655,908 B2 | 2/2014 | Kenedy et al. |
| 8,655,915 B2 | 2/2014 | Kenedy et al. |
| 8,738,297 B2 | 5/2014 | Sorenson |
| 8,786,603 B2 | 7/2014 | Rasmussen |
| 8,788,283 B2 | 7/2014 | Kenedy et al. |
| 8,788,286 B2 | 7/2014 | Kenedy et al. |
| 8,855,935 B2 | 10/2014 | Myres |
| 8,990,250 B1 | 3/2015 | Chowdry et al. |
| 9,031,870 B2 | 5/2015 | Kenedy et al. |
| 9,116,882 B1 | 8/2015 | Macpherson et al. |
| 9,170,992 B2 | 10/2015 | Kenedy et al. |
| 9,213,944 B1 | 12/2015 | Do et al. |
| 9,213,947 B1 | 12/2015 | Do et al. |
| 9,218,451 B2 | 12/2015 | Wong et al. |
| 9,336,177 B2 | 5/2016 | Hawthorne et al. |
| 9,367,663 B2 | 6/2016 | Deciu et al. |
| 9,367,800 B1 | 6/2016 | Do et al. |
| 9,390,225 B2 | 7/2016 | Barber et al. |
| 9,405,818 B2 | 8/2016 | Chowdry et al. |
| 9,582,647 B2 | 2/2017 | Kenedy et al. |
| 9,836,576 B1 | 12/2017 | Do et al. |
| 9,864,835 B2 * | 1/2018 | Avey ....................... G16B 20/20 |
| 9,977,708 B1 | 5/2018 | Do et al. |
| 10,025,877 B2 | 7/2018 | Macpherson |
| 10,162,880 B1 | 12/2018 | Chowdry et al. |
| 10,275,569 B2 * | 4/2019 | Avey ....................... G16B 45/00 |
| 10,296,847 B1 | 5/2019 | Do et al. |
| 10,379,812 B2 | 8/2019 | Kenedy et al. |
| 10,432,640 B1 | 10/2019 | Hawthorne |
| 10,437,858 B2 | 10/2019 | Naughton et al. |
| 10,516,670 B2 | 12/2019 | Hawthorne et al. |
| 10,572,831 B1 | 2/2020 | Do et al. |
| 10,643,740 B2 * | 5/2020 | Avey ....................... G16B 20/40 |
| 10,658,071 B2 | 5/2020 | Do et al. |
| 10,691,725 B2 | 6/2020 | Naughton et al. |
| 10,699,803 B1 | 6/2020 | Do et al. |
| 10,755,805 B1 | 8/2020 | Do et al. |
| 10,777,302 B2 | 9/2020 | Chowdry |
| 10,790,041 B2 | 9/2020 | Macpherson et al. |
| 10,803,134 B2 | 10/2020 | Kenedy et al. |
| 10,841,312 B2 | 11/2020 | Hawthorne et al. |
| 10,854,318 B2 | 12/2020 | Macpherson et al. |
| 10,891,317 B1 | 1/2021 | Chowdry et al. |
| 10,896,233 B2 | 1/2021 | Kenedy et al. |
| 10,936,626 B1 | 3/2021 | Naughton et al. |
| 10,957,455 B2 | 3/2021 | Kenedy |
| 10,991,467 B2 | 4/2021 | Kenedy et al. |
| 10,999,285 B2 | 5/2021 | Hawthorne et al. |
| 11,003,694 B2 | 5/2021 | Kenedy et al. |
| 11,031,101 B2 | 6/2021 | Hon et al. |
| 11,049,589 B2 | 6/2021 | Hon et al. |
| 11,170,047 B2 | 11/2021 | Macpherson |
| 11,170,873 B2 * | 11/2021 | Avey ....................... G16B 45/00 |
| 11,171,962 B2 | 11/2021 | Hawthorne et al. |
| 11,875,879 B1 * | 1/2024 | Avey ....................... G16B 20/20 |
| 2004/0081996 A1 | 4/2004 | Landers |
| 2004/0126840 A1 | 7/2004 | Cheng et al. |
| 2004/0229231 A1 | 11/2004 | Frudakis et al. |
| 2004/0241730 A1 | 12/2004 | Yakhini et al. |
| 2004/0248086 A9 | 12/2004 | Ginns et al. |
| 2005/0089852 A1 | 4/2005 | Lee et al. |
| 2005/0147947 A1 | 7/2005 | Cookson, Jr. et al. |
| 2007/0037182 A1 | 2/2007 | Gaskin et al. |
| 2007/0250809 A1 | 10/2007 | Kennedy et al. |
| 2008/0131887 A1 | 6/2008 | Stephan et al. |
| 2008/0227063 A1 | 9/2008 | Kenedy et al. |
| 2008/0228043 A1 | 9/2008 | Kenedy et al. |
| 2008/0228410 A1 | 9/2008 | Kenedy et al. |
| 2008/0228451 A1 | 9/2008 | Kenedy et al. |
| 2008/0228677 A1 | 9/2008 | Kenedy et al. |
| 2008/0228698 A1 | 9/2008 | Kenedy et al. |
| 2008/0228699 A1 | 9/2008 | Kenedy et al. |
| 2008/0228700 A1 | 9/2008 | Kenedy et al. |
| 2008/0228701 A1 | 9/2008 | Kenedy et al. |
| 2008/0228702 A1 | 9/2008 | Kenedy et al. |
| 2008/0228704 A1 | 9/2008 | Kenedy et al. |
| 2008/0228705 A1 | 9/2008 | Kenedy et al. |
| 2008/0228706 A1 | 9/2008 | Kenedy et al. |
| 2008/0228708 A1 | 9/2008 | Kenedy et al. |
| 2008/0228722 A1 | 9/2008 | Kenedy et al. |
| 2008/0228753 A1 | 9/2008 | Kenedy et al. |
| 2008/0228756 A1 | 9/2008 | Kenedy et al. |
| 2008/0228757 A1 | 9/2008 | Kenedy et al. |
| 2008/0228765 A1 | 9/2008 | Kenedy et al. |
| 2008/0228766 A1 | 9/2008 | Kenedy et al. |
| 2008/0228767 A1 | 9/2008 | Kenedy et al. |
| 2008/0228768 A1 | 9/2008 | Kenedy et al. |
| 2008/0228797 A1 | 9/2008 | Kenedy et al. |
| 2008/0243843 A1 | 10/2008 | Kenedy et al. |
| 2009/0043752 A1 | 2/2009 | Kenedy et al. |
| 2009/0099789 A1 | 4/2009 | Stephan et al. |
| 2009/0112871 A1 | 4/2009 | Hawthorne et al. |
| 2009/0118131 A1 | 5/2009 | Avey et al. |
| 2009/0119083 A1 | 5/2009 | Avey et al. |
| 2010/0042438 A1 | 2/2010 | Moore et al. |
| 2010/0063830 A1 | 3/2010 | Kenedy et al. |
| 2010/0063835 A1 | 3/2010 | Kenedy et al. |
| 2010/0063865 A1 | 3/2010 | Kenedy et al. |
| 2010/0063930 A1 | 3/2010 | Kenedy |
| 2010/0070292 A1 | 3/2010 | Kenedy et al. |
| 2010/0070455 A1 | 3/2010 | Halperin et al. |
| 2010/0076950 A1 | 3/2010 | Kenedy et al. |
| 2010/0076988 A1 | 3/2010 | Kenedy et al. |
| 2010/0169262 A1 | 7/2010 | Kenedy et al. |
| 2010/0169313 A1 | 7/2010 | Kenedy et al. |
| 2010/0169338 A1 | 7/2010 | Kenedy et al. |
| 2010/0223281 A1 | 9/2010 | Hon |
| 2011/0078168 A1 | 3/2011 | Kenedy et al. |
| 2011/0184656 A1 | 7/2011 | Kenedy et al. |
| 2012/0270190 A1 | 10/2012 | Kenedy et al. |
| 2012/0270794 A1 | 10/2012 | Eriksson et al. |
| 2013/0345988 A1 | 12/2013 | Avey et al. |
| 2014/0006433 A1 | 1/2014 | Hon et al. |
| 2014/0067355 A1 | 3/2014 | Noto et al. |
| 2015/0227610 A1 | 8/2015 | Chowdry et al. |
| 2015/0248473 A1 | 9/2015 | Kenedy et al. |
| 2015/0347566 A1 | 12/2015 | Kenedy et al. |
| 2016/0026755 A1 | 1/2016 | Byrnes |
| 2016/0103950 A1 | 4/2016 | Myres et al. |
| 2016/0171155 A1 | 6/2016 | Do et al. |
| 2016/0277408 A1 | 9/2016 | Hawthorne et al. |
| 2016/0350479 A1 | 12/2016 | Han et al. |
| 2017/0011042 A1 | 1/2017 | Kermany et al. |
| 2017/0017752 A1 | 1/2017 | Noto et al. |
| 2017/0053089 A1 | 2/2017 | Kenedy et al. |
| 2017/0185719 A1 | 6/2017 | Kenedy et al. |
| 2017/0220738 A1 | 8/2017 | Barber et al. |
| 2017/0228498 A1 | 8/2017 | Hon et al. |
| 2017/0277827 A1 | 9/2017 | Granka et al. |
| 2017/0277828 A1 | 9/2017 | Avey et al. |
| 2017/0329866 A1 | 11/2017 | Macpherson |
| 2017/0329891 A1 | 11/2017 | Macpherson et al. |
| 2017/0329899 A1 | 11/2017 | Bryc et al. |
| 2017/0329901 A1 | 11/2017 | Chowdry et al. |
| 2017/0329902 A1 | 11/2017 | Bryc et al. |
| 2017/0329904 A1 | 11/2017 | Naughton et al. |
| 2017/0329915 A1 | 11/2017 | Kittredge et al. |
| 2017/0329924 A1 | 11/2017 | Macpherson et al. |
| 2017/0330358 A1 | 11/2017 | Macpherson et al. |
| 2018/0181710 A1 | 6/2018 | Avey et al. |
| 2018/0210705 A1 | 7/2018 | Kenedy |
| 2018/0307778 A1 | 10/2018 | Macpherson |
| 2019/0012431 A1 | 1/2019 | Hon et al. |
| 2019/0034163 A1 | 1/2019 | Kenedy et al. |
| 2019/0114219 A1 | 4/2019 | Do et al. |

(56) References Cited

U.S. PATENT DOCUMENTS

| | | | |
|---|---|---|---|
| 2019/0139623 A1 | 5/2019 | Bryc et al. |
| 2019/0206514 A1 | 7/2019 | Avey et al. |
| 2019/0267115 A1 | 8/2019 | Avey et al. |
| 2019/0281061 A1 | 9/2019 | Hawthorne et al. |
| 2019/0384777 A1 | 12/2019 | Naughton et al. |
| 2020/0137063 A1 | 4/2020 | Hawthorne et al. |
| 2020/0210143 A1 | 7/2020 | Kenedy et al. |
| 2020/0372974 A1 | 11/2020 | Chowdry et al. |
| 2021/0020266 A1 | 1/2021 | Freyman et al. |
| 2021/0043278 A1 | 2/2021 | Hon et al. |
| 2021/0043279 A1 | 2/2021 | Hon et al. |
| 2021/0043280 A1 | 2/2021 | Hon et al. |
| 2021/0043281 A1 | 2/2021 | Macpherson et al. |
| 2021/0058398 A1 | 2/2021 | Hawthorne et al. |
| 2021/0074385 A1 | 3/2021 | Hon et al. |
| 2021/0082167 A1 | 3/2021 | Jewett et al. |
| 2021/0166452 A1 | 6/2021 | Jewett et al. |
| 2021/0166823 A1 | 6/2021 | Kenedy et al. |
| 2021/0193257 A1 | 6/2021 | Freyman et al. |
| 2021/0209134 A1 | 7/2021 | Kenedy et al. |
| 2021/0225458 A1 | 7/2021 | Hon et al. |
| 2021/0233665 A1 | 7/2021 | Kenedy et al. |
| 2021/0243094 A1 | 8/2021 | Holness et al. |
| 2021/0250357 A1 | 8/2021 | Hawthorne et al. |
| 2021/0313013 A1 | 10/2021 | Hon et al. |
| 2021/0375392 A1 | 12/2021 | Polcari et al. |
| 2022/0157405 A1* | 5/2022 | Avey | G16B 20/20 |
| 2024/0112758 A1* | 4/2024 | Avey | G16B 20/20 |

FOREIGN PATENT DOCUMENTS

| | | |
|---|---|---|
| WO | 20060116622 W | 11/2006 |
| WO | WO 2007/084902 | 7/2007 |
| WO | WO 2007/084902 A9 | 7/2007 |
| WO | 2009051768 A1 | 4/2009 |
| WO | WO 2016/073953 | 5/2016 |

OTHER PUBLICATIONS

U.S. Notice of Allowance dated Nov. 26, 2018 in U.S. Appl. No. 12/288,096.
Office Action, U.S. Appl. No. 18/534,002, mailed Oct. 22, 2024.
Caballero V, Preliminary molecular genetic analysis of the Receptor Interacting Protein 140 (RIP140) in women affected by endometriosis. J Exp Clin Assist Reprod. Aug. 30, 2005;2:11. doi: 10.1186/1743-1050-2-11. PMID: 16131398; PMCID: PMC1242355.
Horton R, et al., Gene map of the extended human MHC. Nat Rev Genet. Dec. 2004;5(12):889-99. doi: 10.1038/nrg1489. PMID: 15573121.
Nievergelt CM, Suggestive evidence for association of the circadian genes PERIOD3 and ARNTL with bipolar disorder. Am J Med Genet B Neuropsychiatr Genet. Apr. 5, 2006;141B(3):234-41. doi: 10.1002/ajmg.b.30252. PMID: 16528748; PMCID: PMC2651679.
Office Action, U.S. Appl. No. 16/295,399, mailed Apr. 5, 2023.
Reed DR, Diverse tastes: Genetics of sweet and bitter perception. Physiol Behav. Jun. 30, 2006;88(3):215-26. doi: 10.1016/j.physbeh.2006.05.033. Epub Jun. 19, 2006. PMID: 16782140; PMCID: PMC1698869.
Scuteri A, Genome-wide association scan shows genetic variants in the FTO gene are associated with obesity-related traits. PLoS Genet. Jul. 2007;3(7):e115. doi: 10.1371/journal.pgen.0030115. PMID: 17658951; PMCID: PMC1934391.
U.S. Final Office Action dated Dec. 19, 2011 in U.S. Appl. No. 12/288,096.
U.S. Office Action dated Jul. 21, 2011 in U.S. Appl. No. 12/288,096.
U.S. Office Action dated Jun. 13, 2013 in U.S. Appl. No. 12/288,096.
U.S. Office Action dated Dec. 19, 2013 in U.S. Appl. No. 12/288,096.
U.S. Office Action dated Aug. 6, 2014 in U.S. Appl. No. 12/288,096.
U.S. Final Office Action dated Mar. 19, 2015 in U.S. Appl. No. 12/288,096.
U.S. Office Action dated Jul. 22, 2015 in U.S. Appl. No. 12/288,096.
U.S. Final Office Action dated Jan. 11, 2016 in U.S. Appl. No. 12/288,096.
U.S. Office Action dated Sep. 9, 2016 in U.S. Appl. No. 12/288,096.
U.S. Final Office Action dated Apr. 28, 2017 in U.S. Appl. No. 12/288,096.
U.S. Office Action dated Mar. 13, 2018 in U.S. Appl. No. 12/288,096.
U.S. Notice of Allowance dated Nov. 16, 2018 in U.S. Appl. No. 12/288,096.
U.S. Office Action dated Sep. 17, 2019 in U.S. Appl. No. 16/409,574.
U.S. Notice of Allowance dated Jan. 3, 2020 in U.S. Appl. No. 16/409,574.
U.S. Office Action dated Jul. 21, 2011 in U.S. Appl. No. 12/288,026.
U.S. Final Office Action dated Dec. 19, 2011 in U.S. Appl. No. 12/288,026.
U.S. Office Action dated Oct. 2, 2013 in U.S. Appl. No. 12/288,026.
U.S. Final Office Action dated Apr. 16, 2014 in U.S. Appl. No. 12/288,026.
U.S. Office Action dated Dec. 4, 2014 in U.S. Appl. No. 12/288,026.
U.S. Final Office Action dated May 22, 2015 in U.S. Appl. No. 12/288,026.
U.S. Office Action dated Sep. 9, 2016 in U.S. Appl. No. 12/288,026.
U.S. Final Office Action dated Apr. 27, 2017 in U.S. Appl. No. 12/288,026.
Notice of Allowance dated Sep. 12, 2017 in U.S. Appl. No. 12/288,026.
U.S. Office Action dated Jun. 23, 2020 in U.S. Appl. No. 15/829,782.
U.S. Final Office Action dated Mar. 1, 2021 U.S. Appl. No. 15/829,782.
International Search Report and Written Opinion dated Dec. 10, 2008 in PCT/US2008/11806.
International Preliminary Report on Patentability dated Apr. 29, 2010 in PCT/US2008/011806.
International Search Report and Written Opinion dated Dec. 29, 2008 in PCT/US2008/11833.
International Preliminary Report on Patentability dated Apr. 20, 2010 in PCT/US2008/011833.
Avalos, et al. "Mendelian Inheritance" Encyclopedia of Molecular Biology (2002) pp. 1-4, John Wiley and Sons Inc. ebook. [retrieved Jun. 18, 2020].
PubMed.gov Overview. Downloaded from Pubmed.gov Jun. 18, 2020. eResource. 1 page.
Pearson, W. R., et al. "Improved tools for biological sequence comparison," Proceedings of the National Academy of Sciences (PNAS), Biochemistry, vol. 85, No. 8, Apr. 1, 1988, pp. 2444-2448.
Human Genome Landmarks Poster, United States Department of Energy (DOE), pp. 6. [retrieved Jan. 27, 2007] <URL:http//web.archive.org/web/20070127170426/http://www.ornl.gov/sci/techresources/Human_Genome/posters/chromosome/chooser.shtml>.
Yang, et al., "Linkers: A simulation programming system for generating populations with genetic structure" Computers in Biology and Medicine, vol. 20, No. 2, 1990, pp. 135-144.
Osier, et al., "ALFRED: An allele frequency database for anthropology," American Journal of Physical Anthropology, vol. 119, No. 1, Aug. 14, 2002, pp. 77-83. <doi:10.1002/ajpa.10094>.
Poznik, et al., "A novel framework for sib pair linkage analysis," The American Journal Human Genetics, vol. 78, Feb. 2006, pp. 222-230.
Purcell, et al., "PLINK: A Tool Set for Whole-Genome Association and Population-Based Linkage Analyses," The American Journal of Human Genetics, vol. 81, Sep. 2007, pp. 559-575.
Rao, et al., "SAGE Programs; Model free linkage analysis for complex cardiovascular phentyopes," Methods in Molecular Medicine, vol. 128, chapter 6, (2006) pp. 61-89.
Office Action, U.S. Appl. No. 16/295,399, mailed Oct. 18, 2022.

* cited by examiner

GENETIC COMPARISONS BETWEEN GRANDPARENTS AND GRANDCHILDREN

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in their entireties and for all purposes.

BACKGROUND OF THE INVENTION

The instructions for making the cells in the human body are encoded in deoxyribonucleic acid (DNA). DNA is a long, ladder-shaped molecule, in which each corresponding rung is made up of a pair of interlocking units, called bases, that are designated by the four letters in the DNA alphabet—A, T, G and C. 'A' always pairs with 'T', and 'G' always pairs with 'C'. The sequence of these four letters that make up an individual's DNA is referred to as the individual's genome.

The long molecules of DNA in cells are organized into pieces called chromosomes. Humans have 23 pairs of chromosomes. Other organisms have different numbers of pairs—for example, chimpanzees have 24 pairs. Chromosomes are further organized into short segments of DNA called genes. The different letters A, T, G, and C, which make up a gene, dictates how cells function and what traits to express by dictating what proteins the cells will make. Proteins do much of the work in the body's cells. Some proteins give cells their shape and structure. Others help cells carry out biological processes like digesting food or carrying oxygen in the blood. Using different combinations of the As, Cs, Ts and Gs, DNA creates the different proteins and regulates when and how they are turned on. Information about an individual's DNA sequence, including his or her genome or particular regions of the genome is referred to as genotypic information. Regions of a particular individual's genome can also be referred to as "DNA sequences."

Each person has the same set of genes—about 20,000 in all. The differences between people come from slight variations in these genes. For example, it's not that a person with red hair has the "red hair gene" while a person with brown hair has the "brown hair gene." Rather, all people have genes for hair color, and different versions of these genes, i.e. differences in the regions of the genome containing the gene, dictate whether someone will be a redhead or a brunette.

Variations in DNA sequence can generate biological variations between people by causing differences in the recipes for proteins that are written in genes. Those differences can in turn influence a variety of traits such as appearance, disease susceptibility or response to drugs. While some differences in the DNA sequences among individuals lead to differences in health or physical appearance, some variations in the DNA sequences among individuals seem to lead to no observable differences between people at all.

If one were to compare the DNA of any two people, more than 99% of it is expected to be the same across any appreciable stretch of sequence. However, the less than 1% of the DNA that differs between individuals can add up to many base pairs which contain useful information about the individuals. One can imagine a spectrum, where on one end we have two unrelated people from different ethnic groups. Their DNA will differ a great deal. On the other end of the spectrum we can imagine a pair of very close relatives like a parent and a child or two siblings. When DNA is passed from parent to child it is copied almost exactly. Consequently, virtually one half of the child's DNA will be identical to that of each parent. Similarly, for a pair of siblings, virtually 50% of their DNA should be identical.

Because of recombination of DNA sequences and the independent assortment of chromosomes, the DNA of two parents is shuffled at every generation. That, in addition to the small trickle of new mutations, means that only relatives will carry long genome regions where their DNA is completely or almost completely identical. In order to determine whether a region is identical, one could sequence assay every single base pair directly or assay a large number of markers that vary between individuals. Markers are points along the genome where individuals may differ. These markers could be, but are not limited to, SNPs (Single Nucleotide Polymorphisms), which are points along the genome with two or more common variations. A long stretch of sequence where every marker is the same between two chromosomes indicates that the rest of the sequence, which is not being assayed directly, is also identical. If two markers are same, they are called "Identical By State". If, in addition to being the same, they lie within a region of identical sequence, which is shared because of recent common ancestry, they are "Identical By Descent" or IBD.

Every region of a person's autosomal (restricted to "non-sex" chromosomes) genome is represented by a pair of DNA sequences, one inherited from the mother and one from the father. Therefore, for every person, every marker along the genome (including SNPs) comprises two values where one value is the variant inherited from the mother and one value is the variant inherited from the father. A child inherits virtually 50% of his or her DNA from the father and virtually 50% from the mother. The DNA inherited from the mother can be either inherited from the maternal grandmother or the maternal grandfather. The DNA inherited from the father can be inherited from the paternal grandfather or the paternal grandmother. Because it is useful to know from which grandparent an individual inherited particular genes, it would be useful to have a method for comparing the genotypic information of an individual and his or her grandparents and displaying the comparison in a way that can be easy to understand.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various embodiments of the invention are disclosed in the following detailed description and the accompanying drawings.

FIG. 4 is a screen shot of an example of an interface allowing for receiving an indication that a first individual is a grandparent.

FIG. 6a is a screen shot of an example of an interface displaying a similarity score for a comparison when an indication is received that the comparison should be across all the genome data.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
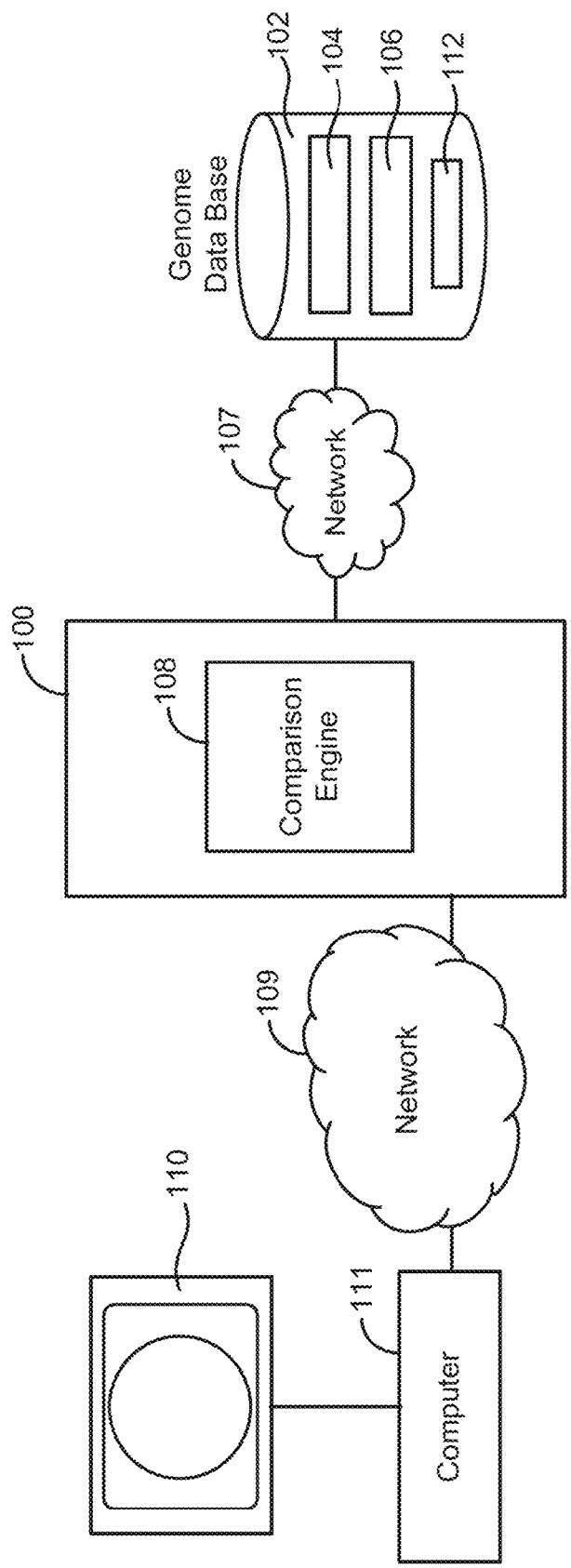
FIG. 1 is a block diagram illustrating an embodiment of a system for displaying similarities in the genotypic data between two individuals.

FIG. 1 is a block diagram illustrating an embodiment of a system for displaying similarities in the genotypic data between two individuals.

In the example shown, system 100 receives an indication of at least two individuals, and then retrieves the genotype information for those individuals. The system 100 may receive an indication that a first individual is a grandparent and that a second individual is a grandchild of the first individual. The system 100 may retrieve the genotypic information for the individuals from a variety of sources. For example, as shown in FIG. 1, the system 100 may be connected, for example by a network 107, to a genome database 102, and retrieve the individual's genotypic information from the database 102, which includes the genotypic information for the first individual 104, the genotypic information for the second individual 106, and the genotypic information for the third individual 112. Alternatively, the genotypic information may be stored in the system 100 or may be received from another source.

The system 100 includes a comparison engine 108 that receives the genotypic information for the at least two individuals 104 and 106 and calculates a similarity score based on the genotypic information. The system may also receive an indication of whether the similarity score should be calculated to determine the similarity across all of the genome data of the individuals or the similarity between the at least two individuals' genome data with respect to a particular trait. The system 100 is connected, for example through a network 109 to a computer 111 which is connected to a display 110, for displaying a representation of the similarity score between or among the at least two individuals. The display 110 can include any device that will allow for displaying a representation of a similarity score, such as a monitor with a web browser.

Figure 2A:
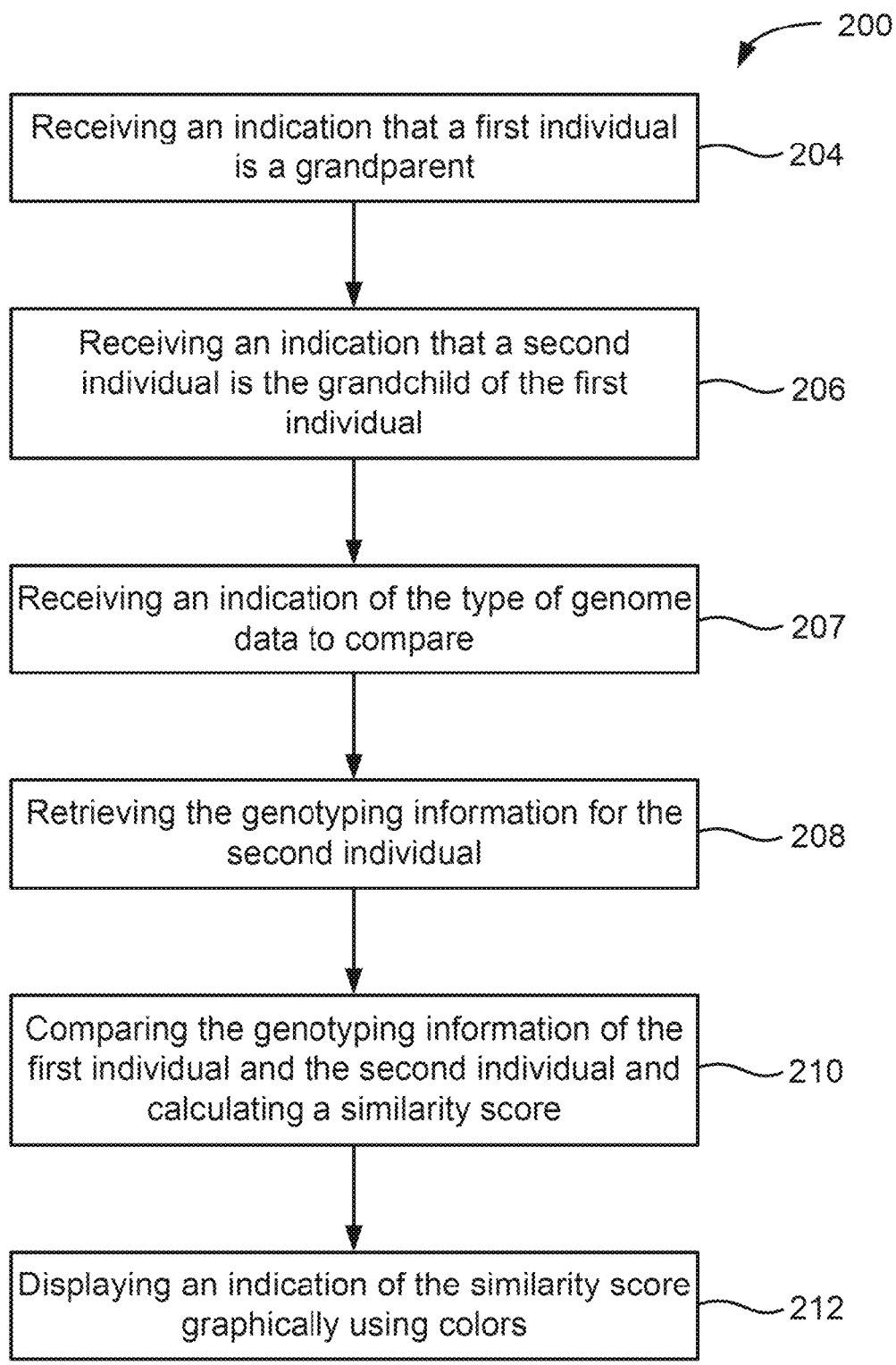
FIG. 2a is a flow chart illustrating an embodiment of a method for displaying similarities in the genotypic data between a grandparent and a grandchild.
Figure 3:
FIG. 3 is a screen shot of an example of an interface displaying the relationships between an individual's grandparent and the individual's parents, and the relationship between the individual's parents and the individual.
Figure 4:
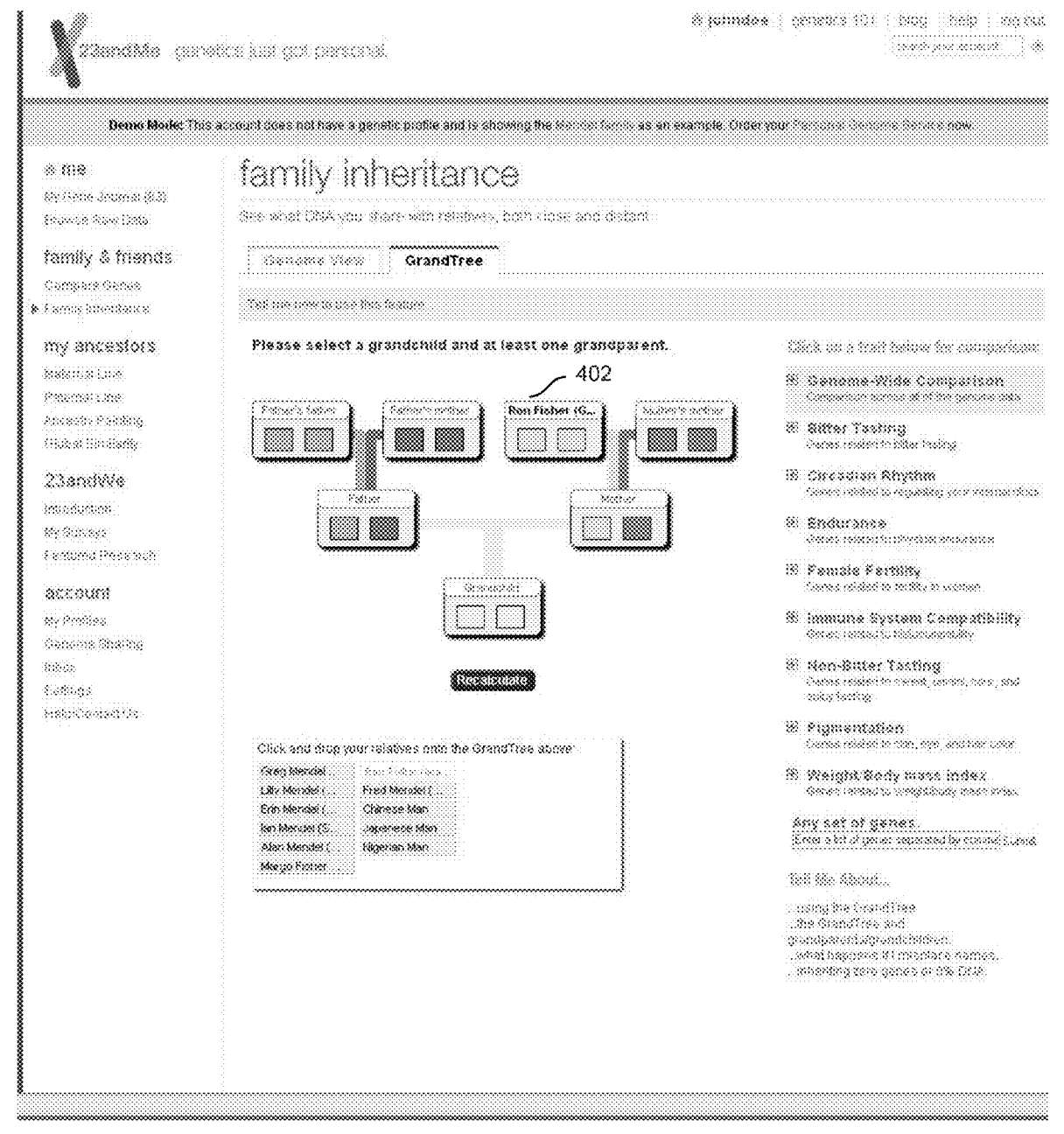

FIG. 2a is a flow chart illustrating an embodiment of a method 200 for displaying similarities in the genotypic data between a grandparent and a grandchild. At 204, an indication that a first individual is a grandparent is received. FIG. 3 is a screen shot of an example of an interface displaying the relationships between an individual's grandparent and the individual's parents, and the relationship between the individual's parents and the individual. The example in FIG. 3 displays the relationship in a graphical tree structure, but other structures could be used. FIG. 4 is a screen shot of an example of an interface allowing for receiving an indication that a first individual is a grandparent. In the example shown in FIG. 4 at 402, "Ron Fisher" is indicated as the maternal grandparent. For example, a user may have selected "Ron Fisher" from a list of relatives and dragged and dropped "Ron Fisher" to the maternal grandfather position in the family tree.

Figure 5:
FIG. 5 is a screen shot of an example of an interface allowing for receiving an indication that a second individual is the grandchild of the first individual.

At 206, an indication that a second individual is the grandchild of the first individual is received. FIG. 5 is a screen shot of an example of an interface allowing for receiving an indication that a second individual is the grandchild of the first individual. In the example shown in FIG. 5 at 502, "Erin Mendel" is indicated as the grandchild of "Ron Fisher." For example, a user may have selected "Erin Mendel" from a list of relatives and dragged and dropped "Erin Mendel" to the grandchild position in the family tree.

At 207, an indication is received of the particular type of genome data for which the genotypic information should be compared. This indication may include a comparison across all of the genome data, or a comparison of the genome data regarding a particular trait. Examples of particular traits may include: bitter tasting, circadian rhythm, endurance, female fertility, immune system compatibility, non-bitter tasting, pigmentation, weight body mass index, or a set of genes indicated by the use. In the example shown in FIG. 4, the indication received is for a comparison across all of the genome data. As the example in FIG. 4 illustrates, a user interface may allow for receiving an indication of the type of genome data by a user clicking on a list on the screen. FIG. 4, however is only one example of allowing for receiving such an indication.

In some embodiments, a user then selects the "Recalculate" button below the family tree. In response, 208-212 are performed. In other embodiments, 208-212 are automatically performed.

At 208, the genotypic information for the first and second individual is retrieved. An example of retrieving the genotypic information is further illustrated in FIG. 1, in which the genotypic information for the first individual 104 and the second individual 106 is retrieved from a Genome Database coupled to the system 100. As discussed above, this is only an example of retrieving genotypic information for individuals. Genotypic information for an individual can be retrieved from other types of sources.

At 210, the genotypic information of the first individual 104 and second individual 106 is compared and a similarity score is calculated. In comparing genotypic information for two individuals, we expect more than 99% of the underlying DNA sequence to be the same. However, the less than 1% of the DNA that may differ represents a large number of base pairs. There may be many base pairs that differ in the DNA of two unrelated people from different ethnic groups. On the other hand, when DNA is passed from parent to child it is copied almost exactly. All locations on an individual's genome are represented by two DNA sequences one inherited from the father and one inherited from the mother. Two individuals are half-identical for a DNA region if one of their two sequences is the same at that region. Two individuals are identical for a DNA region if both of their two sequences are the same at that region. Because children inherit almost exactly 50% of their genomes from each parent, they are considered half-identical across the entire genome to each parent. Because a parent's chromosomes recombine before being passed on to children, a child receives a mixture of his or her grandparents' genomes. For example, because the DNA a mother passes to her daughter is a mixture of DNA from the maternal grandmother and the maternal grandfather, only patches of a grandchild's genome will be half-identical to each grandparent's genome.

In order to determine whether a region is identical, one could assay every single base pair directly or assay a large number of markers that vary between individuals. Markers are points along the genome where individuals may differ. These markers could be SNPs (Single Nucleotide Polymorphisms), which are points along the genome with two or more common variations. A long stretch of sequence where every marker is the same between two people indicates that the rest of the sequence, which is not being assayed directly, is also identical. If two markers are same, they are called "Identical By State". If, in addition to being the same, they lie within a region of identical sequence, which is shared because of recent common ancestry, they are "Identical By Descent" or IBD.

Available genotypic information may come in "phased" or "unphased" forms. As explained above, humans have 23 pairs of chromosomes. Every region of a person's autosomal (restricted to "non-sex" chromosomes) genome is represented by a pair of DNA sequences, one inherited from the mother and one from the father. If the genotypic data is "unphased" then it does not specify whether the marker values come from a particular one of the two pairs of DNA sequences for the chromosomes. With "phased" genotypic data, each of the markers values is specifically associated with one of the two pairs of DNA sequences for the chromosomes. The data can also come in a partially phased form where some of the markers have phased information while others do not. At 210 the comparison can be done using any combination of phased, partially-phased or unphased data.

An example of a way to find DNA regions that are IBD between two people using unphased SNP genotype data is to scan the genome in windows of 10 Centimorgans ("CM"). For every window the method can compare all the SNP values or genotypes between the two people. If every SNP has the same exact values, then the two people are completely identical along the 10 CM window. If they are not all the same, but every SNP has at least one value (allele) in common between two people, then the two people are half-identical along the window. The method can also allow for a small percentage of errors so that not every SNP has to have the same values or some values in common, to make the determination of identity or half-identity, respectively. Other embodiments can include other methods for determining IBD regions. As described above, DNA regions that a grandchild inherited from a grandparent should be IBD when comparing the grandchild's genome to that of the grandparent. Therefore, it can be estimated how much DNA a grandchild inherited from each grandparent, and also which genes come from whom.

Using the retrieved genotypic information for the individuals, a similarity score can be calculated by comparing the first individual's DNA to the second individual's DNA and determining the percentage of the DNA that is half-identical. If an indication is received at 207 that the comparison should be for all genotype data, the similarity score will be the percentage of all of the individual's genome for which data is available that is half-identical. If an indication is received at 207 that the comparison should be made for a particular trait, then only the DNA regions which are relevant to that particular trait are compared and the similarity score is only the percentage of those regions which are half-identical.

As explained above, each genomic region is represented by two DNA sequences, one inherited from the mother and one inherited from the father. Because a grandchild receives DNA sequence for each region from each parent, who received one sequence for each region from each of their parents, a grandchild is half-identical to either one grandparent on one side or the other grandparent on that side for every region along the genome. Thus, if the grandchild is not half-identical to a grandparent along certain regions, the grandchild will be half identical to the other grandparent along those regions. For example, if the maternal grandfather and the grandchild are compared for any regions that are not half-identical, the grandchild will be half-identical to the maternal grandmother along those regions. Thus, once a similarity score has been calculated estimating the inheritance for one grandparent on one side, the similarity score for the other grandparent can be calculated without any genetic comparisons. The similarity score estimating the inheritance for the other grandparent can be calculated by subtracting the first grandparent's similarity score, which is a percentage, from 100, or (100%−(similarity score)).

Figure 6A:
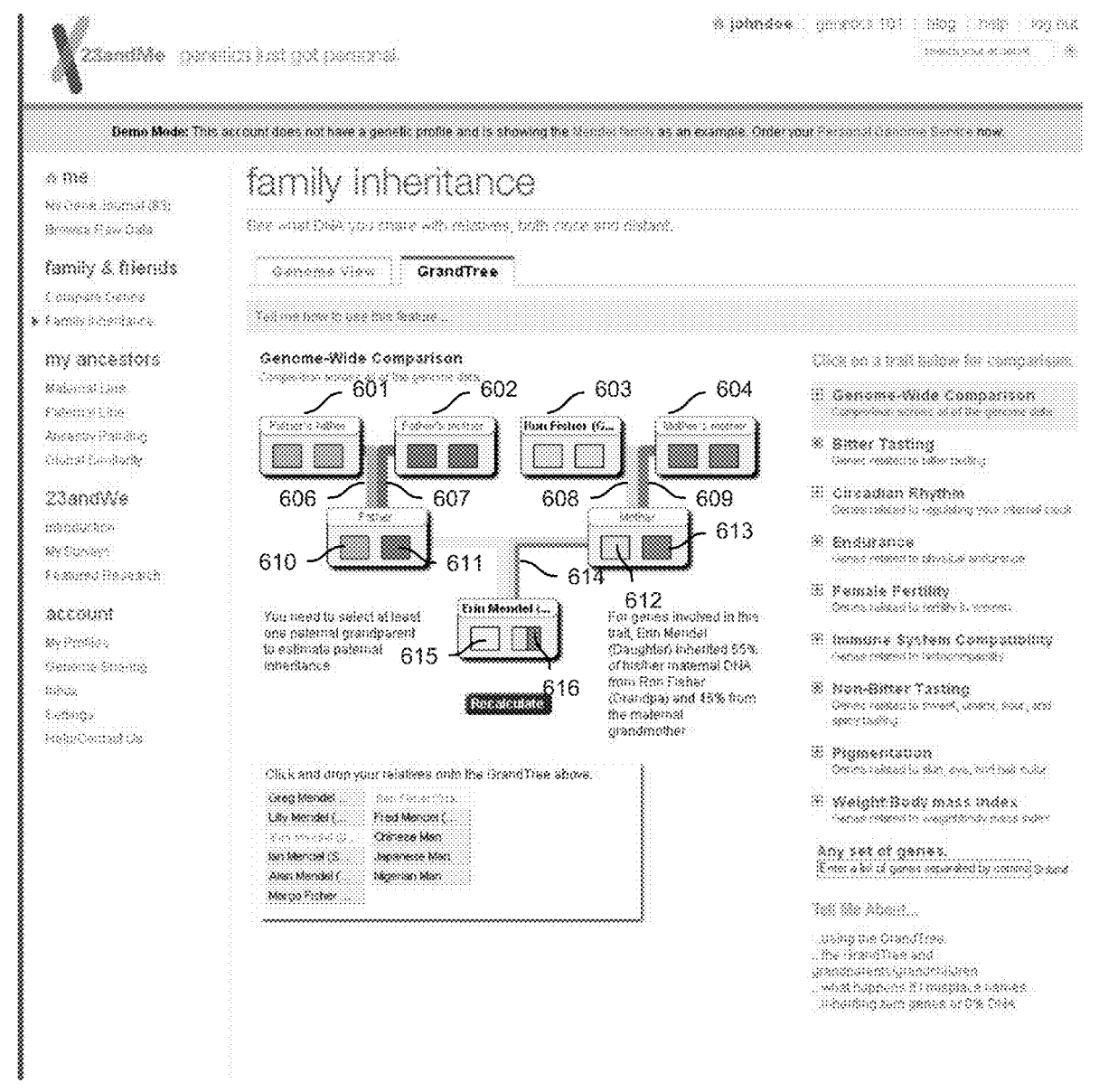

Once this similarity score has been calculated, at 212, an indication of the similarity score between the first individual and the second individual is displayed graphically using colors. FIG. 6a is a screen shot of an example of an interface displaying a similarity score for a comparison when an indication is received in FIG. 2 at 207 that the comparison should be across all the genome data. In the display example shown in FIG. 6a, an indication is received that "Ron Fisher" is the grandfather and that "Erin Mendel" is the grandchild. In the example shown, the color yellow is used to indicate the similarity score between the maternal grandfather and the grandchild. As shown in FIG. 6a, on the maternal side, there is a line drawn between the grandparents and the mother and then a line drawn between the mother and the grandchild. In the indication for each grandparent, there are boxes colored to indicate that person's genome. In the example shown, the boxes for the paternal grandfather 601 are green and the boxes for the paternal grandmother 602 are blue, the boxes for the maternal grandfather 603 are yellow and the boxes for the maternal grandmother 604 are red. To indicate the genetic connection between the grandparents and the parents, a colored line is shown from each grandparent to the parent that is his or her child. The lines 606, 607, 608 and 609 are the same color as the respective boxes 601, 602, 603 and 604 for each respect grandparent. In the example shown in FIG. 6a, 606 is green, 607 is blue, 608 is yellow, and 609 is red. The width of each of these lines indicates the percentage of the genome that is inherited by the parents from each of the respect grandparents. Because each parent inherits half of his or her genome from each of his or her parents, i.e., each parent is virtually half-identical to each grandparent, the lines 606 and 607 between each of the father's parents to the father are the same width. Also, the lines 608 and 609 between each of the mother's parents and the mother are the same width. In FIG. 6a, the boxes for the indication of the father's genome inherited from his parents 610 and 611 are the same color as the lines 606 and 607. Each box is the same size, because an equal amount of the genome was inherited from each parent. In FIG. 6a, the boxes for the indication of the mother's genome inherited from her parents 612 and 613 are the same color as the lines 608 and 609. In this embodiment, each box is the same size, because an equal amount of the genome was inherited from each parent. Because children are half-identical to their parents, no genetic comparisons were needed to display the similarities between the grandparents and the parents.

In the example in FIG. 6a, because an indication was received that "Ron Fisher" is the maternal grandfather of "Erin Mendel," the calculated similarity score can be displayed using the colors for the maternal grandparents. As shown in FIG. 6a, a line 614 is displayed between the mother and the grandchild. The line 614 is a combination of the color for the boxes 603 and 604 for each maternal grandparent. Thus, line 614 is yellow and red. The width of each color in line 614 indicates the similarity score for each grandparent. For example, as shown in FIG. 6a, because the similarity score between the indicated maternal grandfather ("Ron Fisher" in this example) was calculated as 55%, 55% of the line between the mother and the grandchild ("Erin Mendel" in this example) is yellow. Because the resulting similarity score between the maternal grandmother is (100%-55%) or 45% as explained above, 45% of the line is red. Box 616, which further indicates this similarity score, is 55% yellow and 45% red. Because no paternal grandparents were indicated, no similarity score could be calculated, and therefore, no line between the father and the child is displayed and the box 615 for indicating the similarity score for the paternal grandparents is not colored.

Figure 6B:
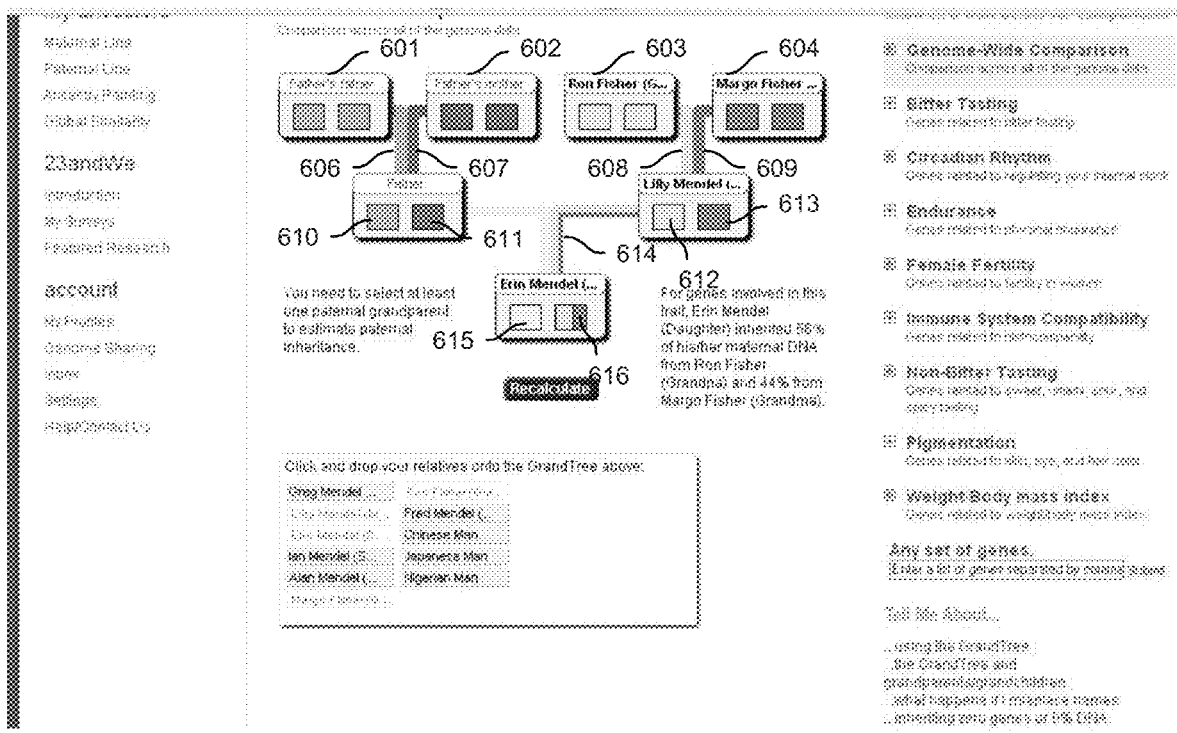
FIG. 6b is a screen shot of the display shown in FIG. 6a when a further indication has been received that a third individual is the other grandparent on the same side and that a fourth individual is the child of the indicated grandparents.

FIG. 6b is a screen shot of the display shown in FIG. 6a when a further indication has been received that a third individual is the other grandparent on the same side and that a fourth individual is the child of the indicated grandparents. In FIG. 6b, an indication that the maternal grandmother is "Margo Fisher" and that the mother is "Lilly Mendel" is received. As explained above, once a similarity score has been computed for one grandparent on one side, the similarity score for the other grandparent on that side can be computed as (100%−(similarity score)). Thus, as shown in the example in FIG. 6b, receiving an indication that a third individual is the grandparent on the same side would not necessarily change the display of the similarity score. In some embodiments, the estimates can be improved when considering this additional indication or other indications. When two colors are used to display the similarity score of one grandparent by illustrating the similarity score in comparison to the similarity score of the other grandparent on that side, receiving a further indication that an individual is a grandparent on the same side as the indicated grandparent does not necessarily change the display in this embodiment. As shown in FIG. 6b, the width of all the colors of the boxes and lines are the same as in FIG. 6a. Because it is known that individuals are half-identical to their parents, receiving an indication of the parent who is the child of a grandparent also does not necessarily change the display when colors are used to display the similarity score.

In some embodiments the estimates of which DNA regions are IBD with different grandparents can be improved by receiving indications of additional relationships. For example, when comparing a grandchild to the maternal grandfather at a particular SNP using unphased data, we might have a value of GG for both the grandchild and the grandfather. That information by itself is not enough to make a determination of whether that SNP is located in a region which is IBD between the grandfather and the grandchild. However, if we also have genotypic data for the maternal grandmother at that SNP and the value for that SNP is AA, then we know that the DNA region around the SNP was not inherited from the grandmother and must have been inherited from the grandfather. This would imply that the region is IBD between the grandchild and the grandfather. Another example where an additional indication could be used to improve IBD estimates is when parental genotypic data is available. As above, we could have the case where for a particular SNP we have a value of GG for both a grandchild and the maternal grandfather. As above, based on that information alone, it is impossible to determine whether the SNP is within a region of IBD between the grandchild and the grandfather. However, if the mother's genotypic data is also available and it indicates a value of AG at that SNP, we can infer that the region surrounding the SNP is IBD between the grandchild and the grandfather. This is so because the mother had to have gotten the G allele from the grandfather which would mean that the A allele must have come from the grandmother. Of the mother's two alleles only one could have been passed to the grandchild, and it must have been the G allele because the child is GG. Thus the grandchild inherited one of their G alleles from the maternal grandfather, implying that the surrounding region is IBD between the grandfather and the grandchild. Another example where additional information can be used to improve IBD estimates is when genotypic data is available from the opposite side of the family tree. For example, when comparing a grandchild to the maternal grandfather at a particular SNP using unphased data, we might have a value of AG for the grandchild and GG for the grandfather. That information by itself is not enough to make a determination of whether that SNP is located in a region which is IBD between the grandfather and the grandchild. However, if the father's genotypic data is also available and it indicates a value of GG at that SNP, we can infer that the region surrounding the SNP is not IBD between the grandchild and the maternal grandfather. This is so because the father must have passed on the G allele to the grandchild, which would mean that the grandchild received the A allele from the maternal side. Because the maternal grandfather has only G alleles for that SNP, he could not have passed on the A allele and thus cannot be IBD with the grandchild. Other examples of making use of additional indications of relationships are possible and not limited to the examples given here.

Figure 2B:
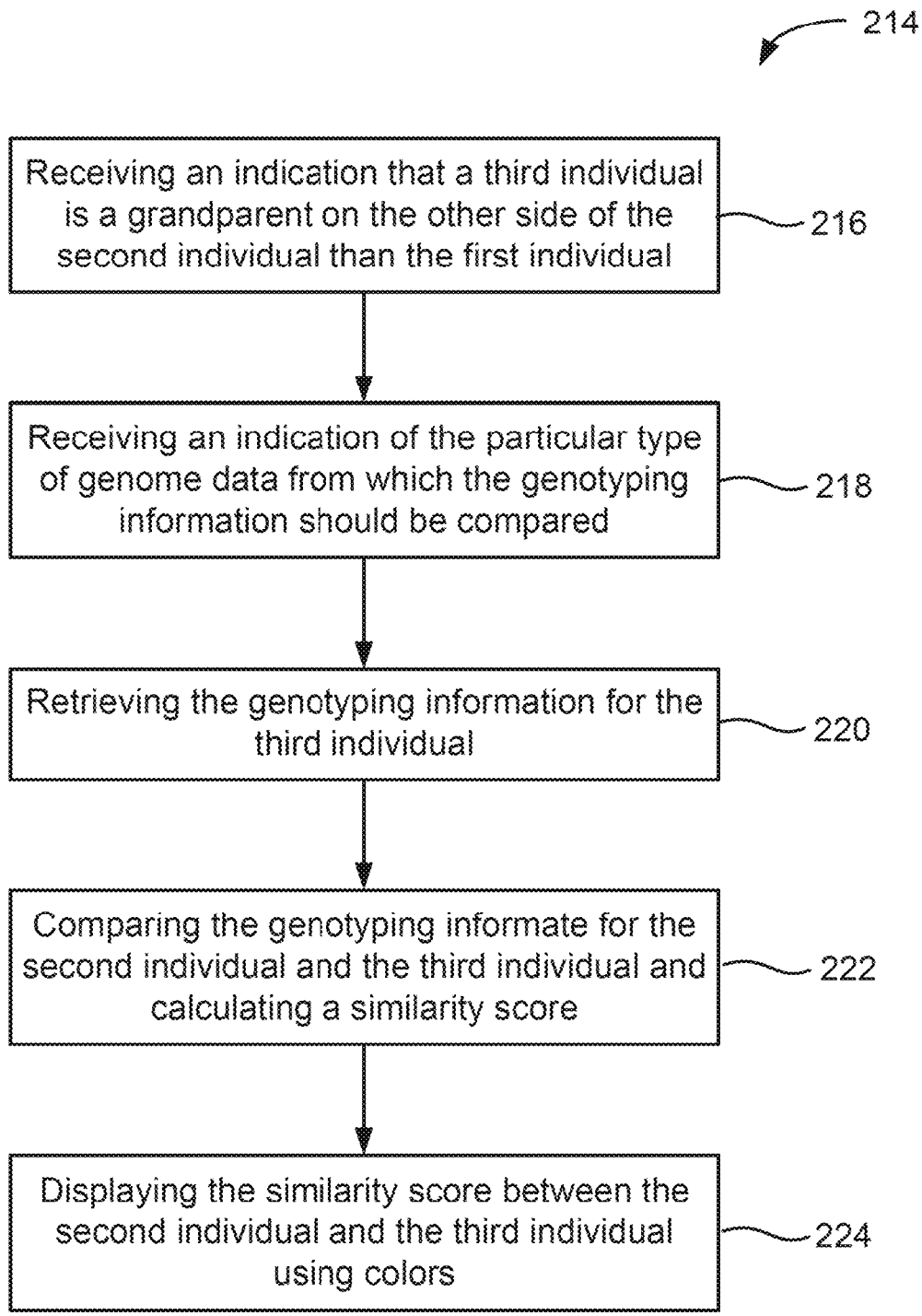
FIG. 2b is a flow chart illustrating an embodiment of a method for displaying similarities in the genotypic data between an additional grandparent and a grandchild.

FIG. 2b is a flow chart illustrating an embodiment of a method 214 for displaying similarities in the genotypic data between an additional grandparent and a grandchild. In some embodiments, the steps in method 214 can occur together with the steps in method 200 illustrated in FIG. 2a. At 216, an indication that a third individual is a grandparent on the other side of the second individual than the first individual is received. At 218, an indication is received of the particular type of genome data for which the genotypic information should be compared. When the method 214 occurs with the steps of the method 200, this step may be omitted. At step 220, the genotypic information for the third individual 112 is retrieved. This step may be performed in the same manner as step 208 described above. At step 222, the genotypic information for the second individual 106 and the third individual 112 is compared and a similarity score is calculated. This step may be performed in the same manner as step 210 described above. In step 224 the similarity score between the second individual and the third individual is displayed using colors.

Figure 6C:
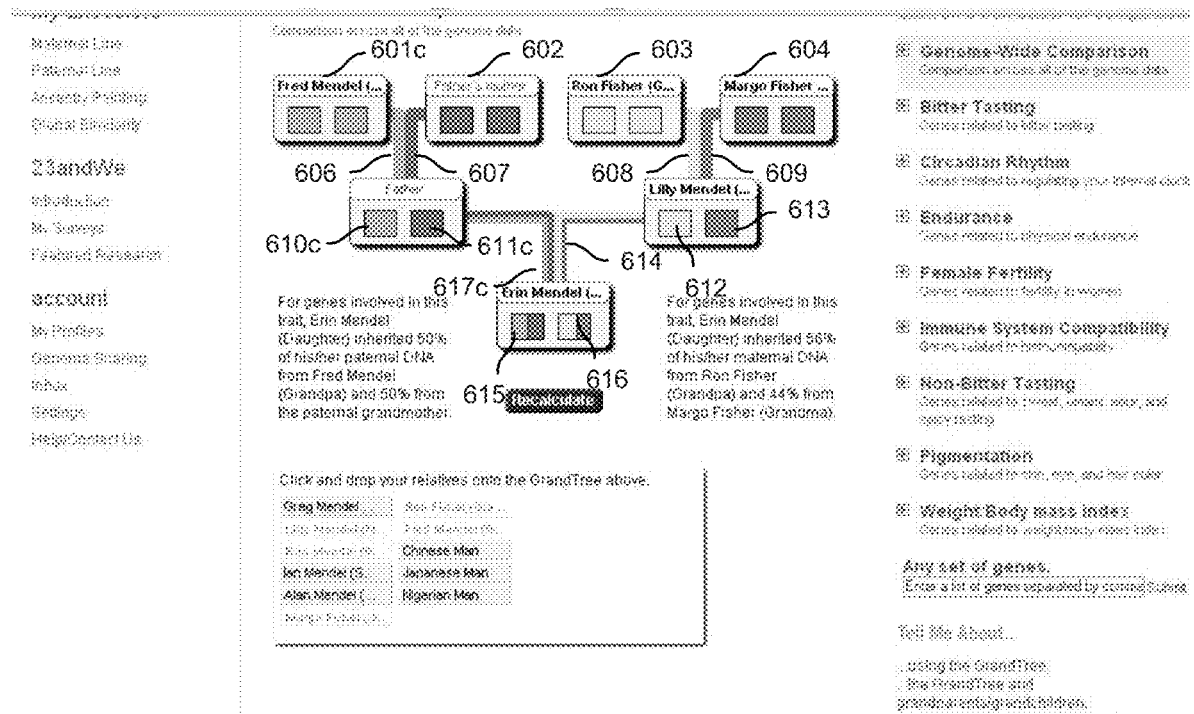
FIG. 6c is a screen shot of an example of an interface displaying an indication of the similarity score displayed in FIG. 6a and displaying an additional similarity score when an indication is received that a third individual is a grandparent on the other side of the first individual.

FIG. 6c is a screen shot of an example of an interface displaying an indication of the similarity score displayed in FIG. 6a and displaying an additional similarity score when an indication is received at 216 that a third individual is a grandparent on the other side of the first individual. In the example shown in FIG. 6c, an indication was received that the comparison should be across all genome data. In the example shown in FIG. 6c, an indication is received that "Ron Fisher" is a maternal grandparent, and an indication is received that "Fred Mendel" is a paternal grandparent. Because the inheritance between the paternal grandparents and the father were known prior to receiving an indication of one of the paternal grandparents, FIG. 6c does not necessarily change from FIG. 6a other than the addition of the line 617 and the coloring of box 615, the box and line displaying an indication of the similarity score between the paternal grandparent, "Fred Mendel", and the grandchild "Erin Mendel." In the display shown in FIG. 6c, green is used to indicate the similarity score between "Fred Mendel" and "Erin Mendel" for a comparison across all genome data. Blue is used to indicate the similarity score between the paternal grandmother and "Erin Mendel" across all genome data. As with line 614 described with respect to FIG. 6a, the percentage of the width of each color in line 617 corresponds to the similarity score for the paternal grandparent associated with that color in this embodiment. Because the grandchild shown in FIG. 6c inherited 50% of all of her genome data from her paternal grandfather and 50% from her paternal grandmother, line 617 is 50% blue and 50% green. The width of each color in box 615 also corresponds to the similarity score for the paternal grandparent associated with that color. In the example in 6c, 50% of box 615 is colored blue and 50% of box 615 is colored green.

Figure 6D:
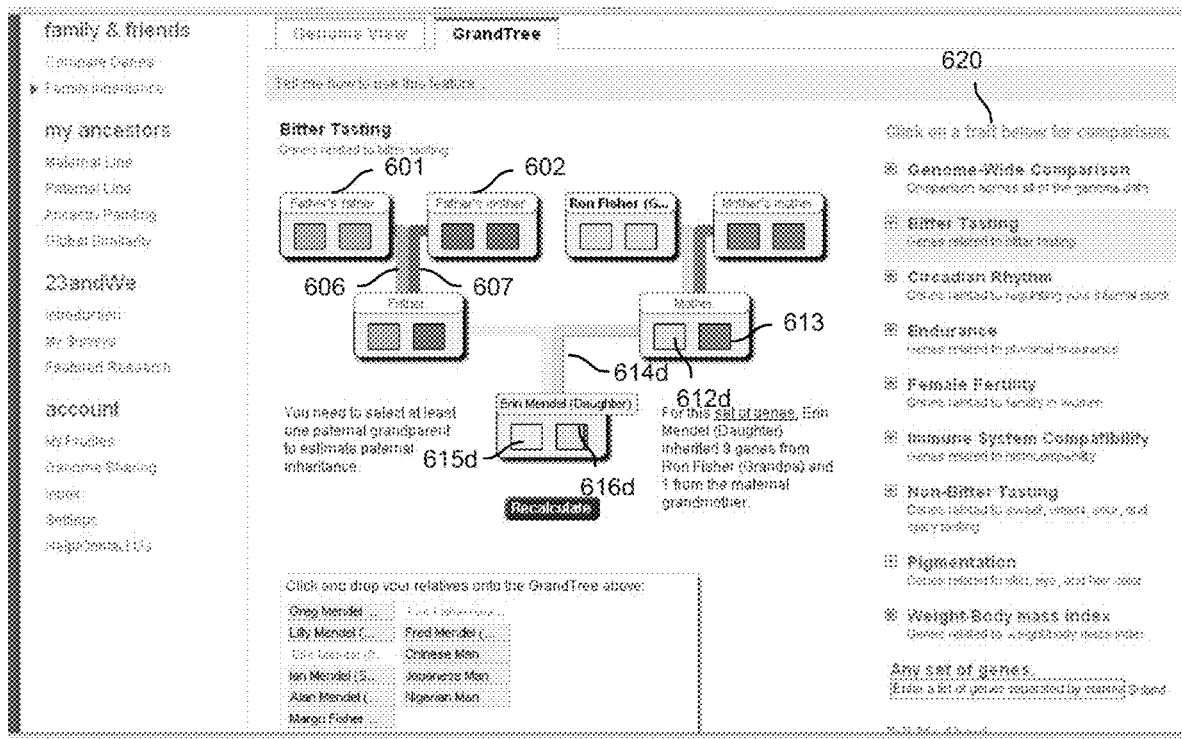
FIG. 6d is a screen shot of an example of an interface displaying a similarity score when an indication is received that the comparison should be for the genome data relating to a particular trait.

FIG. 6d is a screen shot of an example of an interface displaying a similarity score when an indication is received in FIG. 2 at 207 that the comparison should be for the genome data relating to a particular trait. In the example shown in FIG. 6d at 620, one way for an indication to be received that the similarity score should be calculated based on a particular trait is by the user clicking on or otherwise selecting that trait in a list of traits, and then selecting the "Recalculate" button. In the example shown in FIG. 6d at 620, the particular trait is "bitter tasting." For the reason explained above, the genome of each parent is half identical to their parents. Therefore, the aspects of the display showing the inheritance of genes from the grandparents to the parents, the boxes 601-604, 610-613, and the lines 606-608 are the same as the corresponding boxes and lines in FIG. 6a. However, because only the DNA relevant to the genes for the particular trait are compared, the similarity score between the indicated grandparent "Ron Fisher" and the indicated grandchild "Erin Mendel" is different from the similarity score in FIG. 6a, which was calculated across all of the genome data. Therefore, line 614d and box 616d indicating the similarity score for the genome data relating to this particular trait, are different from line 614 and box 616 in FIG. 6a. In the example shown in FIG. 6d, the indicated grandchild inherited 9 of the 10 genes relating to bitter tasting from the indicated grandfather "Ron Fisher" and 1 of the 10 genes from her maternal grandmother. Therefore, line 614d indicating the similarity score between the grandchild and her maternal grandfather (between "Ron Fisher" and "Erin Mendel") is 90% yellow because yellow is used to indicate the similarity score between the maternal grandfather and grandchild for the indicated trait. Line 614d is 10% red because red is used to indicate the similarity score between the maternal grandmother and grandchild. For the same reason, the corresponding box 616d is 90% yellow and 10% red. Because no indication of paternal grandparents was received, there is no line between the father and the child and the box 615 is not colored.

In other embodiments, receiving an indication at 207 of a type of genome data for which the genotypic information should be compared comprises receiving an indication of a user-specified type of genotypic information. For example, the user might type in a particular trait or location on the genome.

It is to be understood that FIGS. 6a-d are only one example of displaying an indication of the similarity score using colors. Other methods of displaying an indication of the similarity score using colors could be used. For example, a display may only include colored lines and not colored boxes. Alternatively, a display may include only boxes and not include lines. Other methods of displaying an indication of the similarity score using colors could be used. In some embodiments, in place of colors, shading or other types of fill (e.g., hatching or cross-hatching) may be used. Additionally, other examples may include displaying an indication of the similarity score between a grandchild and grandparents from generations further back in the individual's ancestral line.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A computer-implemented method for graphically displaying a first estimated amount of genotypic information inherited by a first grandchild from a first grandparent of the first grandchild using a user interface to receive user input and interact with a system or a genome database comprising genotypic information of the first grandchild and the first grandparent, the first grandchild being biologically related to the first grandparent, the method comprising:

(a) causing to be displayed on a display device of a computer system:
a graphical tree structure comprising:
a first grandparent position corresponding to genotypic information of the first grandparent;
a first grandchild position corresponding to genotypic information of the first grandchild;
a first graphically displayed box and/or line for graphically displaying an indication of genotypic information of the first grandparent; and
a second graphically displayed box and/or line configured to be updated to graphically display the first estimated amount of genotypic information inherited by the first grandchild from the first grandparent;
wherein the first and second graphically displayed boxes and/or lines are positioned with respect to one another in the graphical tree structure in a manner depicting a relationship between the first grandchild and the first grandparent;
(b) receiving a user-specified indication of the first grandparent;
(c) receiving a user-specified indication of the first grandchild;
(d) sending to the system or the genome database the user-specified indications of (b) and (c) for each of the first grandchild and the first grandparent;
(e) receiving from the system or the genome database the first estimated amount of genotypic information inherited by the first grandchild from the first grandparent, wherein the first estimated amount is based at least in part on the genotypic information of the first grandparent and the genotypic information of the first grandchild; and
(f) based on the first estimated amount received in (e), causing to be automatically updated the graphical tree structure displayed on the display device, wherein the causing to be automatically updated is performed by a processor configured to update the graphical tree structure, wherein causing to be automatically updated includes causing updating of the second graphically displayed box and/or line to display a graphical indication of the first estimated amount of genotypic information inherited by the first grandchild from the first grandparent, wherein the second graphically displayed box and/or line is updated to be proportional to the first estimated amount of genotypic information inherited by the first grandchild from the first grandparent.

2. The method of claim 1, further comprising:
causing to be displayed on a display device of the computer system a list of types of genome data, wherein the list is configured for receiving, from a user, a user-selected type of genome data for which an estimated amount of inherited genotypic information is to be displayed; and
receiving a selection, from the list displayed on the display device, of the user- selected type of genome data for which the first estimated amount of genotypic information inherited by the first grandchild from the first grandparent is to be displayed on the display device.

3. The method of claim 2, wherein the list of types of genome data is configured for receiving a user-selected type of genome data selected from a group consisting of bitter taste perception, skin pigmentation, weight, and total genome data.

4. The method of claim 2, wherein the list of types of genome data is configured for receiving a user-selected type of genome data selected from a group consisting of genome data across the whole genome, genome data associated with a trait, and genome data associated with at least one gene.

5. The method of claim 4, wherein the trait is selected from the group consisting of bitter tasting, circadian rhythm, endurance, female fertility, immune system compatibility, non-bitter tasting, pigmentation, appearance, and weight body mass index.

6. The method of claim 4, wherein the trait is selected from the group consisting of susceptibility to a disease and response to a drug.

7. The method of claim 1, wherein the graphical tree structure further comprises a first parent position, the first parent being a biological child of the first grandparent and a biological parent of the first grandchild, wherein the first parent position corresponds to genotypic information of the first parent.

8. The method of claim 7, wherein the graphical tree structure further comprises a third graphically displayed box and/or line for graphically displaying an estimated amount of genotypic information inherited by the first parent from the first grandparent.

9. The method of claim 7, further comprising:
(g) receiving a user-specified indication of the first parent, wherein the genome database further comprises genotypic information of the first parent;
(h) receiving the first estimated amount of genotypic information inherited by the first grandchild from the first grandparent, wherein the first estimated amount is based at least in part on the genotypic information for each of the first grandchild and the first grandparent received in (e) and the genotypic information for the first parent; and
(i) based on the first estimated amount received in (h), causing to be automatically updated the graphical tree structure displayed on the display device, wherein causing to be automatically updated causes updating the second graphically displayed box and/or line to display a graphical indication of the first estimated amount of genotypic information inherited by the first grandchild from the first grandparent.

10. The method of claim 1, wherein (e) further comprises receiving a second estimated amount of genotypic information inherited by the first grandchild from a second grandparent, the second grandparent being biologically related to the first grandchild, and wherein, based on at least the first estimated amount, causing to be automatically updated in (f) further comprises causing to be updated the second graphically displayed box and/or line to display a graphical indication of the first estimated amount of genotypic information inherited by the first grandchild from the first grandparent and a graphical indication of the second estimated amount of genotypic information of genome data inherited by the first grandchild from the second grandparent.

11. The method of claim 10, wherein the second graphically displayed box comprises a first area and a second area, the first area being proportional in size to the first estimated amount and the second area being proportional in size to the second estimated amount.

12. The method of claim 11, wherein each of the first area and second area of the second graphically displayed box is displayed in a different color.

13. The method of claim 10, wherein the second graphically displayed line comprises a first line and a second line, the first line representing the first estimated amount and being proportional in width to the first estimated amount and the second line representing the second estimated amount and being proportional in width to the second estimated amount.

14. The method of claim 13, wherein each of the first line and the second line is displayed in a different color.

15. The method of claim 1, wherein:
the graphical tree structure further comprises:
a second grandparent position, the second grandparent being biologically related to the first grandchild, wherein the second grandparent position corresponds to genotypic information of the second grandparent; and
a third graphically displayed box and/or line for graphically displaying an indication of genotypic information of the second grandparent, wherein the first, second, and third graphically displayed boxes and/or lines are positioned with respect to one another in the graphical tree structure in a manner depicting a relationship between the first grandchild, the first grandparent, and the second grandparent; and
the method further comprises:
(g) receiving a user-specified indication of the second grandparent, wherein the genome database further comprises genotypic information of the second grandparent;
(h) receiving a second estimated amount of genotypic information inherited by the first grandchild from the second grandparent, wherein the second estimated amount is based at least in part on the genotypic information of the first grandchild; and
(i) based on the first and second estimated amounts, causing to be automatically updated, the graphical tree structure displayed on the display device, wherein causing to be automatically updated causes updating the second graphically displayed box and/or line to display a graphical indication of each of the first and second estimated amounts.

16. The method of claim 15, wherein the second graphically displayed box comprises a first area and a second area, the first area being proportional in size to the first estimated amount and the second area being proportional in size to the second estimated amount.

17. The method of claim 16, wherein each of the first area and second area is displayed in a different color.

18. The method of claim 1, wherein the first estimated amount of genotypic information inherited by the first grandchild from the first grandparent, as received in (e), was determined by at least one identical by descent (IBD) region shared between the genotypic information of the first grandchild and the genotypic information of the first grandparent.

19. The method of claim 18, wherein the at least one IBD region was determined by determining a region including at least one single nucleotide polymorphism (SNP) marker for which the genotypic information of the first grandchild and the genotypic information of the first grandparent share at least one allele per SNP marker.

20. The method of claim 1, wherein the second graphically displayed line represents the first estimated amount of genotype information inherited by the first grandchild from the first grandparent.

21. The method of claim 1, wherein causing to be automatically updated further comprises displaying a numerical value indicating the first estimated amount of genotypic information inherited by the first grandchild from the first grandparent.

22. A system for graphically displaying a first estimated amount of genotypic information inherited by a first grandchild from a first grandparent of the first grandchild using a user interface, the first grandchild being biologically related to the first grandparent, the system comprising:
a storage device comprising genotypic information pertaining to autosomal chromosomes of a first grandchild and a first grandparent of the first grandchild;
a computer comprising one or more processors and memory, the one or more processors being configured to:
(a) cause to be displayed on a display device:
a graphical tree structure comprising:
a first grandparent position corresponding to genotypic information of the first grandparent;
a first grandchild position corresponding to genotypic information of the first grandchild;
a first graphically displayed box and/or line for graphically displaying an indication of genotypic information of the first grandparent; and
a second graphically displayed box and/or line configured to be updated to graphically display the first estimated amount of genotypic information inherited by the first grandchild from the first grandparent;
wherein the first and second graphically displayed boxes and/or lines are positioned with respect to one another in the graphical tree structure in a manner depicting a relationship between the first grandchild and the first grandparent;
(b) receive a user-specified indication of the first grandparent;
(c) receive a user-specified indication of the first grandchild;
(d) send to the storage device the user-specified indications of (b) and (c) for each of the first grandchild and the first grandparent;
(e) receive from the storage device the first estimated amount of genotypic information inherited by the first grandchild from the first grandparent, wherein the first estimated amount is based at least in part on the genotypic information of the first grandparent and the genotypic information of the first grandchild; and
(f) based on the first estimated amount received in (e), cause to be automatically updated the graphical tree structure displayed on the display device, wherein causing to be automatically updated is performed by a processor configured to update the graphical tree structure, wherein causing to be automatically updated includes causing updating of the second graphically displayed box and/or line to display a graphical indication of the first estimated amount of genotypic information inherited by the first grandchild from the first grandparent, wherein the second graphically displayed box and/or line is updated to be proportional to the first estimated amount of genotypic information inherited by the first grandchild from the first grandparent.

23. The system of claim 22, wherein the one or more processors are further configured to:
cause to be displayed on the display device a list of types of genome data, wherein the list is configured for receiving, from a user, a user-selected type of genome data for which an estimated amount of inherited genotypic information is to be displayed; and
receive a selection, from the list displayed on the display device, of the user- selected type of genome data for which the first estimated amount of genotypic information inherited by the first grandchild from the first grandparent is to be displayed on the display device.

24. The system of claim 23, wherein the list of types of genome data is configured for receiving a user-selected type of genome data selected from a group consisting of bitter taste perception, skin pigmentation, weight, and total genome data.

25. The system of claim 23, wherein the list of types of genome data is configured for receiving a user-selected type of genome data selected from a group consisting of genome data across the whole genome, genome data associated with a trait, and genome data associated with at least one gene.

26. The system of claim 25, wherein the trait is selected from the group consisting of bitter tasting, circadian rhythm, endurance, female fertility, immune system compatibility, non-bitter tasting, pigmentation, appearance, and weight body mass index.

27. The system of claim 25, wherein the trait is selected from the group consisting of susceptibility to a disease and response to a drug.

28. The system of claim 22, wherein the graphical tree structure further comprises a first parent position, the first parent being a biological child of the first grandparent and a biological parent of the first grandchild, wherein the first parent position corresponds to genotypic information of the first parent.

29. The system of claim 28, wherein the graphical tree structure further comprises a third graphically displayed box and/or line for graphically displaying an estimated amount of genotypic information inherited by the first parent from the first grandparent.

30. The system of claim 28, wherein the one or more processors are further configured to:
(g) receive a user-specified indication of the first parent, wherein the storage device further comprises genotypic information of the first parent;
(h) receive the first estimated amount of genotypic information of genome data inherited by the first grandchild from the first grandparent, wherein the first estimated amount is based at least in part on the genotypic information for each of the first grandchild and the first grandparent received in (e) and the genotypic information for the first parent; and
(i) based on the first estimated amount received in (h), cause to be automatically updated the graphical tree structure displayed on the display device, wherein to cause to be automatically updated causes updating the second graphically displayed box and/or line to display a graphical indication of the first estimated amount of genotypic information inherited by the first grandchild from the first grandparent.

31. The system of claim 22, wherein the one or more processors are further configured to:
in (e), receive a second estimated amount of genotypic information inherited by the first grandchild from a second grandparent, the second grandparent being biologically related to the first grandchild, and cause to be updated in (f) the second graphically displayed box and/or line to display a graphical indication of the first estimated amount of genotypic information inherited by the first grandchild from the first grandparent and a graphical indication of the second estimated amount of genotypic information inherited by the first grandchild from the second grandparent.

32. The system of claim 31, wherein the second graphically displayed box comprises a first area and a second area, the first area being proportional in size to the first estimated amount and the second area being proportional in size to the second estimated amount.

33. The system of claim 32, wherein each of the first area and second area of the second graphically displayed box is displayed in a different color.

34. The system of claim 31, wherein the second graphically displayed line comprises a first line and a second line, the first line representing the first estimated amount and being proportional in width to the first estimated amount and the second line representing the second estimated amount and being proportional in width to the second estimated amount.

35. The system of claim 34, wherein each of the first line and the second line is displayed in a different color.

36. The system of claim 22, wherein:
the graphical tree structure further comprises:
a second grandparent position, the second grandparent being biologically related to the first grandchild, wherein the second grandparent position corresponds to genotypic information of the second grandparent; and
a third graphically displayed box and/or line for graphically displaying an indication of genotypic information of the second grandparent, wherein the first, second, and third graphically displayed boxes and/or lines are positioned with respect to one another in the graphical tree structure in a manner depicting a relationship between the first grandchild, the first grandparent, and the second grandparent; and
the one or more processors are further configured to:
(g) receive a user-specified indication of the second grandparent, wherein the storage device further comprises genotypic information of the second grandparent;
(h) receive a second estimated amount of genotypic information inherited by the first grandchild from the second grandparent, wherein the second estimated amount is based at least in part on the genotypic information of the first grandchild; and
(i) based on the first and second estimated amounts, cause to be automatically updated, the graphical tree structure displayed on the display device, wherein to cause to be automatically updated causes updating the second graphically displayed box and/or line to display a graphical indication of each of the first and second estimated amounts.

37. The system of claim 36, wherein the second graphically displayed box comprises a first area and a second area, the first area being proportional in size to the first estimated amount and the second area being proportional in size to the second estimated amount.

38. The system of claim 37, wherein each of the first area and second area is displayed in a different color.

39. The system of claim 22, wherein the first estimated amount of genotypic information inherited by the first grandchild from the first grandparent was determined by at least one identical by descent (IBD) region shared between the genotypic information of the first grandchild and the genotypic information of the first grandparent.

40. The system of claim 39, wherein the at least one IBD region was determined by determining a region including at least one single nucleotide polymorphism (SNP) marker for which the genotypic information of the first grandchild and the genotypic information of the first grandparent share at least one allele per SNP marker.

41. The system of claim 22, wherein the second graphically displayed line represents the first estimated amount of genotype information inherited by the first grandchild from the first grandparent.

42. The system of claim 22, wherein the one or more processors are further configured to display a numerical value indicating the first estimated amount of genotypic information inherited by the first grandchild from the first grandparent.

\* \* \* \* \*